United States Patent [19]

Kraatz et al.

[11] Patent Number: 4,978,382

[45] Date of Patent: Dec. 18, 1990

[54] PESTICIDES BASED ON 2-HALOGENOALKYLTHIO-SUBSTITUTED PYRIMIDINE DERIVATIVES

[75] Inventors: Udo Kraatz, Leverkusen; Ernst Kysela, Bergisch Gladbach; Jürgen Hartwig, Leverkusen; Benedikt Becker, Mettmann, all of Fed. Rep. of Germany

[73] Assignee: Bayer Aktiengesellschaft, Leverkusen, Fed. Rep. of Germany

[21] Appl. No.: 408,850

[22] Filed: Sep. 18, 1989

[30] Foreign Application Priority Data

Sep. 24, 1988 [DE] Fed. Rep. of Germany ....... 3832530
Apr. 13, 1989 [DE] Fed. Rep. of Germany ....... 3912155

[51] Int. Cl.$^5$ .................. C07D 239/38; A01N 43/54
[52] U.S. Cl. ......................................... 71/92; 544/315
[58] Field of Search ........................... 544/315; 71/92

[56] References Cited

U.S. PATENT DOCUMENTS 3,557,112 1/1971 D'Amico et al. .................. 544/315
4,438,117 3/1984 Cherkofsku ........................ 544/315

FOREIGN PATENT DOCUMENTS 0033195 8/1981 European Pat. Off. .
3510178 9/1986 Fed. Rep. of Germany .

OTHER PUBLICATIONS

Chemical Abstracts, vol. 83, No. 9, Sep. 1, 1975 (79188n) Difluoromethylation of Mercapto Derivatives of Pyrimidine.
European Search Report.

*Primary Examiner*—Mukund J. Shah
*Assistant Examiner*—C. L. Cseh
*Attorney, Agent, or Firm*—Sprung Horn Kramer & Woods

[57] ABSTRACT

A method of combating pests which comprises applying to such pests or to a pest habitat a pesticidally effective amount of a 2-halogenoalkylthio-substituted pyrimidine of the formula

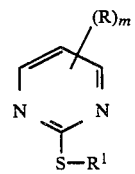

(I)

in which
$R^1$ represents halogenoalkyl,
R represents hydrogen, alkyl, alkylthio, alkoxy, halogenoalkyl, halogenoalkylthio, halogenoalkoxy, optionally substituted aryl or halogen and
m represents a number 0, 1, 2 or 3.

Those compounds other than 2-(difluoromethylthiomethylthio)-4,6-dimethyl-pyrimidine, 2,4-bis(difluoromethylthio)-6-methylpyrimidine and 4-(difluoromethoxy)-2-(difluoromethylthio(-6-methylpyrimidine are new.

15 Claims, No Drawings

PESTICIDES BASED ON 2-HALOGENOALKYLTHIO-SUBSTITUTED PYRIMIDINE DERIVATIVES

The invention relates to the use of 2-halogenoalkylthio-substituted pyrimidine derivatives, some of which are known, as active compounds in pesticides, novel 2-halogenoalkylthio-substituted pyrimidine derivatives, and a process for the preparation thereof.

It has already been disclosed that 2-halogenoalkylthio-substituted pyridines, such as, for example, 2-(dibromofluoromethylthio)-pyridine, possess insecticidal properties (cf. DE-A No. 3,510,178).

However, the action of these compounds is not always entirely satisfactory in all fields of application, in particular at low application rates and application concentrations.

Furthermore, 2-halogenoalkylthio-substituted pyrimidines, such as, for example, 2-(chloromethylthio)-5-chloropyrimidine and 2-(iodomethylthio)-5-chloropyrimidine, are known as intermediates for the preparation of pharmaceutical products (cf. EP-A No. 0,033,195).

In addition, 2-substituted thio-4,5-diarylpyrimidines are known, such as, for example, 2-(1,1,2,2-tetrafluoromethylthio)-4,5-bis(4-methoxyphenyl)-pyrimidine and 2-trifluoromethylthio-4,5-bis(4-fluorophenyl)-pyrimidine. These compounds have, inter alia, a powerful anti-inflammatory and analgesic action (cf. U.S. Pat. No. 4,438,117).

Moreover, a large number of syntheses for 2-halogenoalkylthio-substituted pyrimidine derivatives are known (cf. J. Heterocycl. Chem., 23, 1079–84; J. Heterocyl. Chem. 22, 1077–80; J. Chem. Soc., Perkin Trans., 1, 2499–503; Chem. Scr., 20, 11–13; Deposited Doc., VINITI 910, 5; Zh. Org. Khim., 15, 396–400; J. Org. Chem., 42, 3094–3096; Ukr. Khim. Zh. 42, 500–504; Ukr. Khim. Zh. 41, 498–500; Khim. Geterotsihl. Soedin., 1087–1088).

No biological actions are described for these compounds.

It has been found that the 2-halogenoalkylthio-substituted pyrimidine derivatives, some of which are known, of the general formula (I)

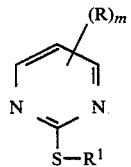

in which
R$^1$ represents halogenoalkyl,
R represents hydrogen, alkyl, alkylthio, alkoxy, halogenoalkyl, halogenoalkylthio, halogenoalkgxy, optionally substituted aryl or halogen, and
m represents a number 0, 1, 2 or 3,
are highly effective against animal pests, in particular against insects, arachnids and nematodes. They are therefore suitable as active compounds in pesticides, in particular as insecticides, acaricides and nematicides.

Surprisingly, the 2-halogenoalkylthio-substituted pyrimidine derivatives of the general formula (I) which are to be used according to the invention show a better action as pesticides, in particular as insecticides, acaricides and nematicides, than 2-(dibromo-fluoromethylthio)-pyridine, which is known from the prior art.

The 2-halogenoalkylthio-substituted pyrimidine derivatives which are to be used according to the invention therefore represent a valuable enrichment of the art.

Formula (I) provides a general definition of the 2-halogenoalkylthio-substituted pyrimidine derivatives to be used according to the invention. Compounds of the formula (I) which are preferably used as pesticides are those in which
R$^1$ represents halogenoalkyl having 1 or 2 carbon atoms and 1 to 5 identical or different halogen atoms,
represents hydrogen, in each case straight-chain or branched alkyl, alkylthio, alkoxy, halogenoalkyl, halogenoalkylthio or halogenoalkoxy, in each case having 1 to 4 carbon atoms and, in the case of halogenoalkyl, halogenoalkylthio and halogenoalkoxy, having 1 to 9 identical or different halogen atoms, furthermore represents phenyl which is optionally monosubstituted or polysubstituted by identical or different substituents from the series comprising halogen, nitro, alkyl or alkoxy, in each case having 1 to 4 carbon atoms, or halogenoalkyl having 1 to 4 carbon atoms and 1 to 9 identical or different halogen atoms, or also represents halogen, and
m represents a number 0, 1, 2 or 3.

Compounds of the formula (I) which are particularly preferably used are those in which
R$^1$ represents halogenomethyl having 1 to 3 identical or different halogen atoms,
R represents hydrogen, methyl, ethyl, n- or i-propyl, n-, i-, s- or t-butyl, methylthio, methoxy, halogenoalkyl, halogenoalkylthio or halogenoalkoxy, in each case having 1 to 2 carbon atoms and 1 to 5 identical or different halogen atoms; furthermore represents phenyl which is optionally monosubstituted to trisubstituted by identical or different substituents from the series comprising fluorine, chlorine, bromine, nitro, methyl, ethyl, methoxy, ethoxy or trifluoromethyl, or also represents halogen, and
m represents a number 0, 1, 2 or 3.

Some of the 2-halogenoalkylthio-substituted pyrimidine derivatives of the formula (I) which are to be used according to the invention are known (cf. J. Heterocycl. Chem., 23, 1079–84; J. Heterocyl. Chem. 22, 1077–80; J. Chem. Soc., Perkin Trans., 1, 2499–503; Chem. Scr., 20, 11–13; Deposited Doc., VINITI 910, 5; Zh. Org. Khim., 15, 396–400; J. Org. Chem., 42, 3094–3096; Ukr. Khim. Zh. 42, 500–504; Ukr. Khim. Zh. 41, 498–500; Khim. Geterotsihl. Soedin., 1087–1088; EP-OS No. 0,033,195 and U.S. Pat. No. 4,438,117).

Substituted 2-halogenomethylthio)-pyrimidine derivatives of the formula (Ia)

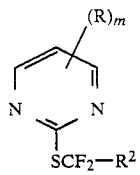

in which

R represents hydrogen, alkyl, alkylthio, alkoxy, halogenoalkyl, halogenoalkylthio, halogenoalkoxy, optionally substituted aryl, or represents halogen, m represents a number 0, 1, 2 or 3 and $R^2$ represents hydrogen, chlorine, bromine or iodine, with the exception of the compounds 2-(difluoromethylthio)-4,6-dimethyl-pyrimidine, 2,4-bis(difluoromethylthio)-6-methyl-pyrimidine and 4-(difluoromethoxy)-2-(difluoromethylthio)-6-methyl-pyrimidine, were hitherto unknown.

Formula (Ia) provides a general definition of the 2-halogenoalkylthio-substituted pyrimidine derivatives according to the invention Preferred compounds of the formula (Ia) are those in which R represents hydrogen, in each case straight-chain or branched alkyl, alkylthio, alkoxy, halogenoalkyl, halogenoalkylthio or halogenoalkoxy, each having 1 to 4 carbon atoms and, in the case of halogenoalkoxyl, halogenoalkylthio and halogenoalkoxy, having 1 to 9 identical or different halogen atoms, furthermore represents phenyl which is optionally monosubstituted or polysubstituted by identical or different substituents from the series comprising halogen, nitro, alkyl or alkoxy, each having 1 to 4 carbon atoms, or halogenoalkyl having 1 to 4 carbon atoms and 1 to 9 identical or different halogen atoms, or also represents halogen, $R^2$ represents hydrogen, chlorine or bromine and m represents a number 0, 1, 2 or 3, with the exception of the compounds 2-(difluoromethylthio)-4,6-dimethyl-pyrimidine, 2,4-bis(difluoromethylthio)-6-methylpyrimidine and 4-(difluoromethoxy)-2-(difluoromethylthio)-6-methylpyrimidine Particularly preferred compounds of the formula (Ia) are those in which R represents hydrogen, methyl, ethyl, n- or i-propyl, n-, i-, s- or t-butyl, methylthio, methoxy, halogenoalkyl, halogenoalkylthio or halogenoalkoxy, each having 1 to 2 carbon atoms and 1 to 5 identical or different halogen atoms; furthermore represents phenyl which is optionally monosubstituted to trisubstituted by identical or different substituents from the series comprising fluorine, chlorine, bromine, nitro, methyl, ethyl, methoxy, ethoxy or trifluoromethyl, or also represents halogen, $R^2$ represents hydrogen, chlorine or bromine and m represents a number 0, 1, 2 or 3, with the exception of the compounds 2-(difluoromethylthio)-4,6-dimethyl-pyrimidine, 2,4-bis(difluoromethylthio)-6-methyl-pyrimidine and 4-(difluoromethoxy)-2-(difluoromethylthio)-6-methyl-pyrimidine.

The substituted 2-(halogenomethylthio)-pyrimidine derivatives of the formula (Ia), which were hitherto unknown, are obtained when 2-mercaptopyrimidines of the formula (II)

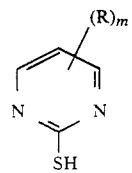

(II)

in which

R and the index m have the abovementioned meanings, or the salts thereof, are alkylated with alkyl halides of the formula (III)

$$R^2-CF_2-X \qquad (III)$$

in which $R^2$ has the abovementioned meaning and

X represents halogen, preferably chlorine or bromine, if appropriate in the presence of diluents and if appropriate in the presence of strong bases.

The known compounds of the formula (I) may be prepared analogously to the process indicated above, for the preparation of the novel compounds of the formula (Ia).

If, for example, 2-mercaptopyrimidine and dibromodifluoromethane are used as starting substances, the course of the reaction of the preparation process may be represented by the following equation:

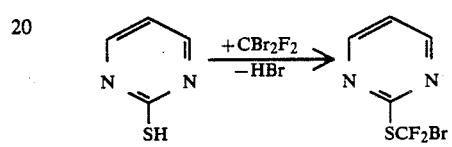

Formula (II) provides a general definition of the 2-mercaptopyrimidines required as starting materials for carrying out the preparation process In this formula (II), R and the index m represent those meanings which have been indicated above in the description of the novel 2-(halogenomethylthio)-pyrimidine derivatives of the formula (Ia) for R and the index m.

The 2-mercaptopyrimidines of the formula (II) are known and/or can be prepared in a simple, analogous manner by known processes (cf. Coll. Czech. Chem. Commun., 24, 1667 (1959); Chem. Ber. 104, 2975 (1971) and U.S. Pat. No. 4,438,117).

Formula (III) provides a general definition of the alkyl halides furthermore required as starting materials for carrying out the preparation process. In this formula (III), $R^2$ and X have those meanings which have been indicated above in the description of the novel 2-(halogenomethylthio)-pyrimidine derivatives of the formula (Ia) for $R^2$ and X.

The compounds of the formula (III) are generally known compounds of organic chemistry.

The novel compounds of the formula (Ia) are preferably prepared using diluents.

Suitable diluents in this process are water and virtually all inert organic solvents which are customary for the reaction. These preferably include aliphatic and aromatic, optionally halogenated hydrocarbons, such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers, such as diethyl ether and dibutyl ether, glycol dimethyl ether and diglycol dimethyl ether, tetrahydrofuran and dioxane, ketones, such as acetone, methyl ethyl ketone, methyl isopropyl ketone and methyl isobutyl ketone, esters, such as methyl acetate and ethyl acetate, nitriles, such as acetonitrile and propionitrile, alcohols, such as methanol, ethanol, n-propanol, isopropanol and butanol, amides, such as, for example, dimethylformamide, dimethylacetamide and N-methyl-pyrrolidone, and also dimethyl sulphoxide, tetramethylene sulphone and hexamethylphosphoric triamide.

Possible bases which are employed in excess are alkali metal hydroxides, such as, for example, sodium hydroxide and potassium hydroxide, alkaline earth metal hydroxides, such as, for example, calcium hydroxide, alkali metal carbonates and alkali metal alcoholates, such as sodium carbonate and potassium carbonate, sodium methylate, potassium methylate, sodium ethylate and potassium ethylate, hydrides, such as, for example, sodium hydride, furthermore aliphatic, aromatic or heterocyclic amines, for example triethylamine, trimethylamine, dimethylaniline, dimethylbenzylamine, pyridine, 1,5-diazabicyclo-[4,3,0]-non-5-ene (DBU), 1,8-diazabicyclo-[5,4,0]-undec-7-ene (DBU) and 1,4-diazabicyclo-[2,2,2]-octane (DABCO).

In the process for the preparation of the novel compounds of the formula (Ia), the reaction temperatures can be varied in a relatively wide range. In general, the process is carried out at temperatures between 0° C. and 100° C., preferably at temperatures between 10° C. and 70° C.

For carrying out the preparation process of the novel compounds of the formula (Ia), 1.0 to 10.0 moles, preferably 1.0 to 6.0 moles, of alkylating agent of the formula (III) and 1.0 to 8.0 moles, preferably 1.0 to 5.0 moles, of base are generally employed per mole of 2-mercaptopyrimidine of the formula (II).

The process for the preparation of the novel compounds of the formula (Ia) is generally carried out under atmospheric pressure. Under certain conditions, however, the process can also be carried out under increased or reduced pressure.

If gaseous alkylating agents of the formula (III) are used, these compounds can be passed in through the mixture of diluent, compound of the formula (II) and base. In general, the reactions are carried out in a suitable diluent, and the reaction mixture is stirred for several hours at the particular temperature required The reaction products of the formula (Ia) are worked up and isolated in a generally customary manner.

The preparation and the use of the active compounds according to the invention can be seen from the following examples.

PREPARATION EXAMPLES

EXAMPLE 1

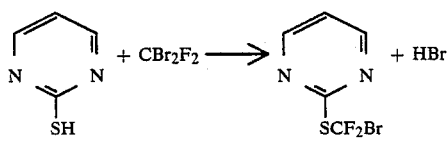

7.5 g (0.25 mol) of sodium hydride (80% strength oil suspension) are added in portions at 20°-30° C. to a stirred solution of 11.2 g (0.1 mol) of 2-mercaptopyrimidine in 200 ml of dimethylformamide. After the mixture has been stirred for 30 minutes at 20° C., 96 g (0.45 mol) of dibromodifluoromethane are added, and stirring is continued overnight, likewise at 20° C. The dimethylformamide is removed under reduced pressure at 20°-30° C., the residue is treated with methylene chloride/water, and the organic phase is separated off. After the organic phase has been dried over magnesium sulphate, the solvent is removed under reduced pressure, and the residue is distilled.

15.2 g (25% of theory) of 2-(bromodifluoromethylthio)-pyrimidine of boiling point bp 100° C./0.3 mm are obtained.

EXAMPLE 2

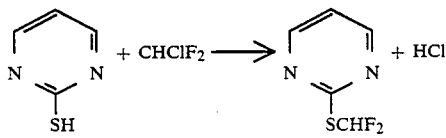

At 40°-50° C., 100 g (1.2 mol) of chlorodifluoromethane are passed into a stirred solution of 25 g (0.22 mol) of 2-mercaptopyrimidine in 120 ml of isopropanol and 30 g (0.73 mol) of sodium hydroxide in 45 ml of water. The reaction is slightly exothermic After the reaction is complete, the mixture is diluted with approximately 400 ml of water, and the product is extracted using methylene chloride. The organic phase is concentrated under reduced pressure, and the residue is distilled under reduced pressure.

17.7 g (49.7% of theory) of 2-(difluoromethylthio)-pyrimidine of boiling point bp 95° C./20 mm are obtained.

The compounds of the formula (I) which are mentioned in the following Table 1 can be prepared analogously to Examples 1 and 2, i.e. the process according to the invention:

TABLE 1

| Example No. | $(R)_m$ structure | $R^1$ | Physical constants |
|---|---|---|---|
| 3 | H$_3$C, H$_3$C substituted pyrimidine | —CF$_2$—Br | $n_D^{20}$: 1.5255 |
| 4 | H$_3$C, H$_3$C substituted pyrimidine | —CF$_2$—Br | $n_D^{24}$: 1.5168 |
| 5 | H$_3$C, H$_5$C$_2$ substituted pyrimidine | —CF$_2$—Br | $n_D^{24}$: 1.5055 |

TABLE 1-continued $$\begin{array}{c}(R)_m\\ \diagup\!\!\!\diagdown\\ N\quad N\\ \diagdown\!\!\!\diagup\\ S-R^1\end{array}\quad (I)$$

| Example No. | (structure) | $R^1$ | Physical constants |
|---|---|---|---|
| 6 | H3C-pyrimidinyl | —CF2—Br | $n_D^{22}$: 1.5230 |
| 7 | H3C-, BrF2CO-pyrimidinyl | —CF2—Br | $n_D^{20}$: 1.4700 |
| 8 | H3C-, F3CS-pyrimidinyl | —CF2—Br | $n_D^{22}$: 1.4970 |
| 9 | H3C-, H3C-pyrimidinyl | —CF2—H | $n_D^{23}$: 1.4994 |
| 10 | H3C-pyrimidinyl | —CF2—H | $n_D^{23}$: 1.5034 |
| 11 | Cl-pyrimidinyl | —CF2—H | b.p. 45° C./ 0.1 mbar |
| 12 | Br-pyrimidinyl | —CF2—H | m.p.: 48° C. |
| 13 | H3C-pyrimidinyl | —CF2—H | m.p.: 47° C. |
| 14 | Br-pyrimidinyl | —CF2—Br | m.p.: 80° C. |
| 15 | Cl-pyrimidinyl | —CF2—Br | $n_D^{23}$: 1.5420 |
| 16 | H3C-pyrimidinyl | —CF2—Br | $n_D^{23}$: 1.5258 |
| 17 | pyrimidinyl | —CF3 | b.p.: 120° C./ 220 mbar |
| 18 | CH3S-pyrimidinyl | —CHF2 | m.p.: 42° C. |
| 19 | CH3O-pyrimidinyl | —CF2Br | m.p.: 40° C. |
| 20 | CH3O-pyrimidinyl |  |  |

The active substances are suitable for combating animal pests, preferably arthropods and nematodes, in particular insects and arachnids, which occur in agriculture, in forestry, in the protection of stored products and of materials, and in the hygiene field They are active against normally-sensitive and resistant species, and against all or individual development stages. The above-mentioned pests include:

From the order of the Isopoda, for example, *Oniscus asellus, Armadillidium vulgare* and *Porcellio scaber.*

From the order of the Diplopoda, for example, *Blaniulus guttulatus.*

From the order of the Chilopoda, for example, *Geophilus carpophagus* and *Scutigera spec.*

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Blatta orientalis, Periplaneta americana, Leucophaea made-* rae, *Blattella germanica, Acheta domesticus,* Gryllotalpa spp., *Locusta migratoria migratorioides, Melanoplus differentialis* and *Schistocerca gregaria.*

From the order of the Dermaptera, for example, *Forficula auricularia.*

From the order of the Isoptera, for example, Reticulitermes spp.

From the order of the Anoplura, for example, *Phylloxera vastatrix,* Pemphigus spp., *Pediculus humanus corporis,* Haematopinus spp. and Linognathus spp.

From the order of the Mallophaga, for example, Trichodectes spp. and Damalinea spp.

From the order of the Thysanoptera, for example, *Hercinothrips femoralis* and *Thrips tabaci.*

From the order of the Heteroptera, for example, Eurygaster spp., *Dysdercus intermedius, Piesma quadrata, Cimex lectularius, Rhodnius prolixus* and Triatoma spp.

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.

From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp. *Bucculatrix thurberiella, Phyllocnistis citrella,* Agrotis spp., Euxoa spp., Feltia spp., *Earias insulana,* Heliothis spp., *Spodoptera exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Tineola bissilliella, Tinea pellionella, Hofmannophila pseudospretella, Cacoecia podana, Capua reticulana, Choristoneura fumiferana, Clysia ambiguella, Homona magnanima* and *Tortrix viridana.*

From the order of the Coleoptera, for example, *Anobium punctatum, Rhizopertha dominica, Acanthoscelides obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varive stis,* Atomaria spp., *Oryzaephilus surinamensis,* Antho nomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Cono derus spp., *Melolontha melolontha, Amphimallon solsti tialis* and *Costelytra zealandica.*

From the order of the Hymenoptera, for example, *Diprion* spp., Hoplocampa spp., Lasius spp., *Monomorium pharaonis* and Vespa spp.

From the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa.*

From the order of the Siphonaptera, for example, *Xenopsylla cheopis* and Ceratophyllus spp..

From the order of the Arachnida, for example, *Scorpio maurus* and *Latrodectus mactans.*

From the order of the Acarina, for example, *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp..

The plant-parasitic nematodes include Pratylenchus spp., *Radopholus similis, Ditylenchus dipsaci, Tylenchulus semipenetrans,* Heterodera spp., Meloidogyne spp., Aphelenchoides spp., Longidorus spp., Xiphinema spp. and Trichodorus spp..

The active compounds of the formula (I) to be used according to the invention are distinguished by an excellent insecticidal activity. In particular, for example, the excellent action against nematodes, such as, for example, Globodera rostochiensis and Meloidogyne incognita, is noteworthy. Moreover, the active compounds according to the invention also show an excellent action against plant-damaging insects, such as, for example, Tetranychus species and Plutella caterpillars.

The active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations are produced in known manner, for example by mixing the active compounds with extenders, that is, liquid solvents, liquefied gases under pressure, and/or solid carriers, optionally with the use of surface-active agents, that is emulsifying agents and/or dispersing agents and/or foam-forming agents. In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as finely divided silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumin hydrolysates; as dispersing agents there are suitable: for example lignin-sulphite waste liquors and methylcellulose.

Adhesives such as carboxym-ethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds to be used according to the invention can be present in their commercially available formulations and in the use forms, prepared from these formulations, as a mixture with other active compounds, such as insecticides, pheromones, sterilizing agents, acaricides, nematicides, fungicides, growth-regulating substances or herbicides. The insecticides include, for example, phosphoric acid esters, carbamates, carboxylates, chlorinated hydrocarbons, phenylureas and substances produced by microorganisms, inter alia.

The active compounds to be used according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene pests and pests of stored products, the active compounds are distinguished by an excellent residual action on wood and clay as well as a good stability to alkali on limed substrates.

The biological effectiveness of the compounds to be used according to the invention will be explained with reference to the examples below.

USE EXAMPLES

In the following Use Examples, the compound mentioned below is employed as comparison substance:

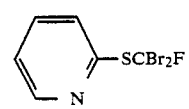

(A)

2-(dibromo-fluoromathylthio)-pyridine.

Compound (A) is disclosed in DE-A No. 2,510,178.

EXAMPLE A

Test nematode: Meloidogyne incognita
Solvent: 3 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

The preparation of active compound is intimately mixed with soil which is heavily infested with the test nematodes. The concentration of the active compound in the preparation is of practically no importance here, only the amount of active compound per unit volume of soil, which is given in ppm, being decisive. The treated soil is filled into pots, lettuce is sown and the pots are kept at a greenhouse temperature of 27° C.

After four weeks, the lettuce roots are examined for infestation with nematodes (root galls), and the degree of effectiveness of the active compound is determined in %. The degree of effectiveness is 100% if infestation is completely avoided and is 0% if the infestation is just as high as in the case of the control plants in untreated soil which has been infested in the same manner.

In this test, for example, the following compounds of Preparation Examples 1, 3, 4, 5, 6, 13, 14, 15 and 16 show a superior effectiveness compared with the prior art:

TABLE A

| Nematicides *Meloidogyne incognita* | |
|---|---|
| Active compound | Degree of destruction in % at an active compound concentration in ppm |
| ⟨pyridine⟩—SCBr₂F (known) (A) | 20 ppm = 0% |
| ⟨pyrimidine⟩—SCF₂—Br (1) | 20 ppm = 100% |
| H₃C-⟨dimethylpyrimidine⟩—SCF₂—Br (3) | 20 ppm = 95% |

TABLE A-continued

Nematicides
*Meloidogyne incognita*

| Active compound | Degree of destruction in % at an active compound concentration in ppm |
|---|---|
| 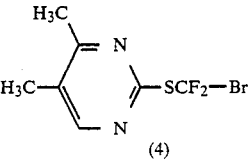 (4) | 20 ppm = 100% |
| 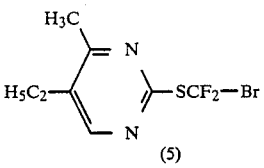 (5) | 20 ppm = 95% |
| 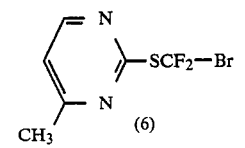 (6) | 20 ppm = 95% |
| 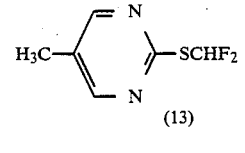 (13) | 20 ppm = 0% |
| 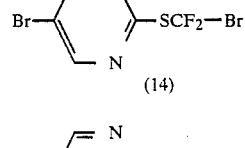 (14) | 20 pm = 100% |
| 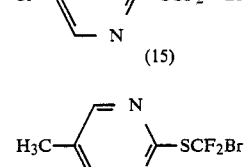 (15) | 20 ppm = 100% |
| 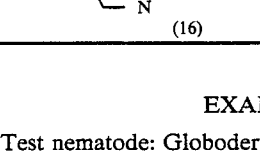 (16) | 20 ppm = 100% |

EXAMPLE B

Test nematode: Globodera rostochiensis
Solvent: 3 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

The preparation of active compound is intimately mixed with soil which is heavily infested with the test nematodes. The concentration of the active compound in the preparation is of practically no importance here, only the amount of active compound per unit volume of soil, which is given in ppm, being decisive. The treated soil is filled into pots, potatoes are planted and the pots are kept at a greenhouse temperature of 18° C.

After six weeks, the potato roots are examined for cysts, and the degree of effectiveness of the active compound is determined in %. The degree of effectiveness is 100% if infestation is completely avoided and is 0% if the plants in untreated soil which has been infested in the same manner.

In this test, for example the following compounds of Preparation Examples 1, 4, 5, 6, 14 and 15 show a superior effectiveness compared with the prior art:

TABLE B

Nematicides
*Globodera rostochiensis*

| Active compound | Degree of destruction in % at an active compound concentration in ppm |
|---|---|
| 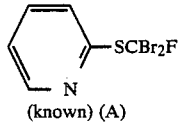 (known) (A) | 20 ppm = 0% |
| 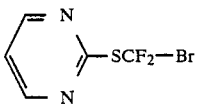 (1) | 20 ppm = 100% |
| 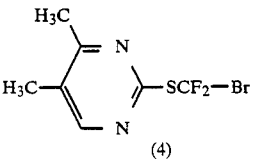 (4) | 20 ppm = 100% |
| 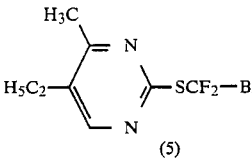 (5) | 20 ppm = 100% |
| 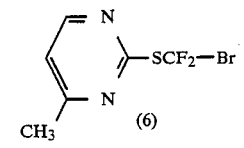 (6) | 20 ppm = 95% |
| 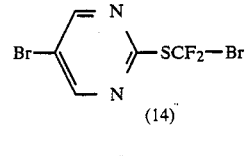 (14) | 20 ppm = 100% |
| 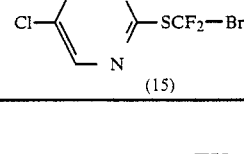 (15) | 20 ppm = 100% |

EXAMPLE C

Tetranychus test (resistant)
Solvent: 3 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Bean plants (*Phaseolus vulgaris*) which are heavily infested with all developmental stages of the common spider mite or greenhouse red spider mite (*Tetranychus urticae*) are treated by dipping into the active compound preparation of the desired concentration.

After the desired time, the destruction is determined in 100% means that all the spider mites have been killed; 0% means that none of the spider mites have been killed.

In this test, for example the following compound of Preparation Example 4 shows a superior effectiveness compared with the prior art.

TABLE C (plant-damaging mites)
Tetranychus (resistant)

| Active compound | Active compound concentration in % | Degree of destruction in % after 7 d |
|---|---|---|
| 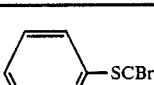 (known) (A) | 0.1 | 0 |
| 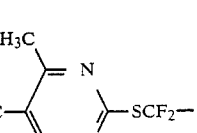 (4) | 0.1 | 95 |

EXAMPLE D

Plutella test
Solvent: 3 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of active compound of the desired concentration and are infested with caterpillars of the diamond-back moth (*Plutella maculipennis*), as long as the leaves are still moist.

After the desired time, the destruction in % is determined. 100% means that all the caterpillars have been killed; 0% means that none of the caterpillars have been killed.

In this test, for example the following compounds of Preparation Examples 1, 4 and 5 show a superior effectiveness compared with the prior art:

TABLE D (plant-damaging insects)
Plutella test

| Active compound | Active compound concentration in % | Degree of destruction in % after 3 d |
|---|---|---|
| 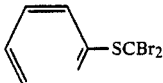 (known) (A) | 0.1 | 0 |
| 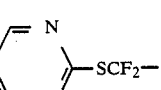 (1) | 0.1 | 100 |
| 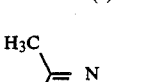 (4) | 0.1 | 100 |
| 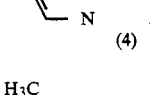 (5) | 0.1 | 100 |

EXAMPLE E

Critical concentration test/soil insects
Test insect: Diabrotica balteata-larvae in the soil
Solvent: 3 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration. The preparation of active compound is intimately mixed with the soil. The concentration of the active compound in the preparation is practically immaterial, the only decisive factor being the amount by weight of active compound per unit volume of soil, which is quoted in ppm (=mg/l). The soil is filled into 0.5 l pots and the pots are left to stand at 20° C.

Immediately after the start of the test 6 pregerminated corn seeds are planted in each of the pots. After 2 days the appropriate test insects are inserted into the treated soil. After further 7 days the degree of effectiveness of the active compound is determined in % by counting the dead and the live test insects. The degree of effectiveness is 100% if all of the test insects have been killed and 0% if exactly as many insects are still alive as in the case of the untreated control.

In this test, for example, the following compounds of preparative examples 2, 7, 8, 10, 14 and 15 display superior effectiveness to the prior art.

TABLE E soil insecticides
*Diabrotica balteata* - larvae in the soil

| Active compound | Degree of destruction in % at an active compound concentration in ppm |
|---|---|
| ![structure](SCBr2F on pyridine) (known) (A) | 20 ppm = 0% |
| F3CS-/pyrimidine-SCHF2, CH3 (known) (8) | 20 ppm = 100% |
| H3C-/pyrimidine-SCF2Br, OCF2Br (7) | 20 ppm = 100% |
| pyrimidine-SCHF2 (2) | 20 ppm = 100% |
| H3C-pyrimidine-SCHF2 (10) | 20 ppm = 100% |
| Br-pyrimidine-SCF2Br (14) | 20 ppm = 100% |
| Cl-pyrimidine-SCF2Br (15) | 20 ppm = 100% |

It is understood that the specification and examples are illustrative but not limitative of the present invention and that other embodiments with the spirit and scope of the invention will suggest themselves to those skill in the art.

We claim:

1. A method of combating pests which comprises applying to such pests or to a pest habitat a pesticidally effective amount of a 2-halogenoalkylthio-substituted pyrimidine of the formula

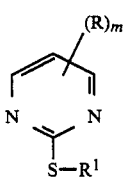

in which
R$^1$ represents halogenoalkyl having 1 or 2 carbon atoms and 1 to 5 identical or different halogen atoms,
R represents hydrogen, in each case straight-chain or branched alkyl, alkylthro, alkoxy, halogenoalkyl, halogenoalkylthio or halogenoalkoxy, in each case having 1 to 4 carbon atoms and, in the case of halogenoalkyl, halogenoalkylthio and halogenoalkoxy, having 1 to 9 identical or different halogen atoms, or represents phenyl which is optionally substituted by identical or different substituents selected from the group consisting of halogen, nitro, alkyl and alkoxy in each case having 1 to 4 carbon atoms, or halogenoalkyl having 1 to 4 carbon atoms and 1 to 9 identical or different halogen atoms, or halogen and
m represents a number 0, 1, 2 or 3.

2. The method according to claim 1, in which
R$^1$ represents halogenomethyl having 1 to 3 identical or different halogen atoms,
R represents hydrogen, methyl, ethyl, n- or i-propyl, n-, i-, s- or t-butyl, methylthio, methoxy, halogenoalkyl, halogenalkylthio or halogenoalkoxy, in each case having 1 to 2 carbon atoms and 1 to 5 identical or different halogen atoms; or represents phenyl which is optionally monosubstituted to trisubstituted by identical or different substituents from the group consisting of fluorine, chlorine, bromine, nitro, ethyl, ethyl, methoxy, ethoxy and trifluoromethyl, or represents halogen, and
m represents a number 0, 1, 2 or 3.

3. The method according to claim 1, in which R$^1$ is CF$_2$Br.

4. The method according to claim 1, wherein such compound is 2-(bromodifluoromethylthio)- pyrimidine of the formula

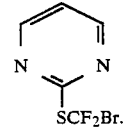

5. The method according to claim 1, wherein such compound is 2-(bromodifluoromethylthio)-4-methyl-5-trifluoromethylthio-pyrimidine of the formula

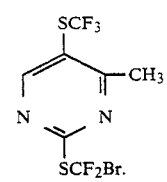

6. The method according to claim 1, wherein such compound is 2-(bromodifluoromethylthio)-5-bromo-pyrimidine of the formula

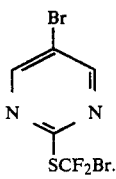

7. The method according to claim 1, wherein such compound is 2-(bromodifluoromethylthio)-5-chloro-pyrimidine of the formula

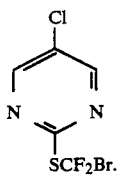

8. A substituted 2-(halogenomethylthio)-pyrimidine of the formula

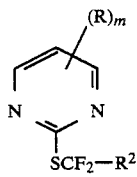
(Ia)

in which
R represents hydrogen, in each case straight-chain or branched alkyl, alkylthio, alkoxy, halogenoalkyl, halogenoalkylthio or halogenoalkoxy, each having 1 to 4 carbon atoms and, in the case of halogenoalkyl, halogeno alkylthio and halogenoalkoxy, having 1 to 9 identical or different halogeno atoms, or represents phenyl which is optionally substituted by identical or different substituents from the group consisting of halogen, nitro, alkyl and alkoxy each having 1 to 4 carbon atoms, or halogenoalkyl having 1 to 4 carbon atoms and 1 to 9 identical or different halogen atoms, or represents halogen,
m represents a number 0, 1, 2 or 3 and
$R^2$ represents hydrogen, chlorine, bromine or iodine, with the exception of the compounds 2-(difluoromethylthio)-4,6-dimethyl-pyrimidine, 2,4-bis(difluoromethylthio)-6-methyl-pyrimidine and 4-(difluoromethoxy)-2-difluoromethylthio)-6-methyl-pyrimidine.

9. A substituted 2-(halogenomethylthio)-pyrimidine according to claim 8, in which
R represents hydrogen, methyl, ethyl, n- or i-propyl, n-, i-, s- or t-butyl, methylthio, methoxy, halogenoalkyl, halogenoalkylthio, halogenoalkoxy, each having 1 to 2 carbon atoms and 1 to 5 identical or different halogen atoms; or represents phenyl which is optionally monosubstituted to trisubstituted by identical or different substituents from the group consisting of fluorine, chlorine, bromine, nitro, methyl, ethyl, methoxy, ethoxy and trifluoromethyl, or represents halogen,
$R^2$ represents hydrogen, chlorine or bromine and
m represents a number 0, 1, 2 or 3, with the exception of the compounds 2-(difluoromethylthio)-4,6-dimethyl-pyrimidine, 2,4-bis(difluoromethylthio)-6-methyl-pyrimidine and 4-(difluoromethoxy)-2-(difluoromethylthio)-6-methyl-pyrimidine.

10. A substituted 2-(halogenomethylthio)-pyrimidine according to claim 8, in which $R^1$ is $CF_2Br$.

11. A compound according to claim 8, wherein such compound is 2-(bromodifluoromethylthio)- pyrimidine of the formula

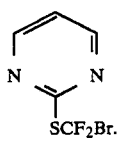

12. A compound according to claim 8, wherein such compound is 2-(bromodifluoromethylthio)-4-methyl-5-trifluoromethylthio-pyrimidine of the formula

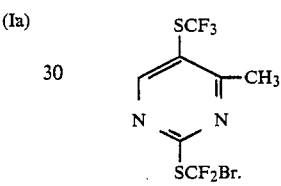

13. A compound according to claim 8, wherein such compound is 2-(bromodifluoromethylthio)-5-bromo-pyrimidine of the formula

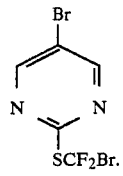

14. A compound according to claim 8 wherein such compound is 2-(bromodifluoromethylthio)-5-chloro-pyrimidine of the formula

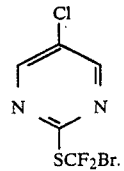

15. A pesticidal composition comprising a pesticidally effective amount of a compound according to claim 8 and a diluent.

* * * * *